US012112479B2

(12) United States Patent
Koike

(10) Patent No.: US 12,112,479 B2
(45) Date of Patent: Oct. 8, 2024

(54) IMAGE PROCESSING DEVICE, IMAGE PROCESSING METHOD, AND IMAGE PROCESSING PROGRAM

(71) Applicant: FUJIFILM CORPORATION, Tokyo (JP)

(72) Inventor: Takafumi Koike, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 459 days.

(21) Appl. No.: 17/683,256

(22) Filed: Feb. 28, 2022

(65) Prior Publication Data

US 2022/0309671 A1 Sep. 29, 2022

(30) Foreign Application Priority Data

Mar. 29, 2021 (JP) ................................. 2021-056179

(51) Int. Cl.
*G06T 7/00* (2017.01)
*A61B 6/00* (2006.01)
(Continued)

(52) U.S. Cl.
CPC .......... *G06T 7/0014* (2013.01); *A61B 6/5217* (2013.01); *A61B 6/025* (2013.01);
(Continued)

(58) Field of Classification Search
CPC ....... G06T 7/0012; G06T 7/0014; G06T 7/30; G06T 7/33; G06T 7/337; G06T 7/60;
(Continued)

(56) References Cited

U.S. PATENT DOCUMENTS

2009/0123052 A1 5/2009 Ruth et al.
2010/0104148 A1* 4/2010 Bovik et al. .............. G06T 5/20
382/128
(Continued)

FOREIGN PATENT DOCUMENTS

JP 2003-260044 A * 9/2003 ............... A61B 6/00
JP 2014-128716 A 7/2014
(Continued)

OTHER PUBLICATIONS

Van Schie, Guido et al., "Mass detection in reconstructed digital breast tomosynthesis volumes with a computer-aided detection system trained on 2D mammograms", Medical Physics, AIP, Melville, NY, US, vol. 40, No. 4, Apr. 1, 2013, pp. 41902-41902.
(Continued)

*Primary Examiner* — Andrew W Johns
(74) *Attorney, Agent, or Firm* — SOLARIS Intellectual Property Group, PLLC

(57) ABSTRACT

An image processing device detects a spicula candidate region having a radial line structure from each of a plurality of tomographic images indicating a plurality of tomographic planes of an object and determines whether or not the spicula candidate region is a spicula on the basis of an amount of change of a center position of the line structure included in the spicula candidate region between the tomographic planes.

7 Claims, 12 Drawing Sheets

(51) Int. Cl.
*A61B 6/02* (2006.01)
*A61B 6/50* (2024.01)

(52) U.S. Cl.
CPC ..... *A61B 6/502* (2013.01); *G06T 2207/10081* (2013.01); *G06T 2207/30068* (2013.01)

(58) Field of Classification Search
CPC .... G06T 7/66; G06T 7/70; G06T 7/73; G06T 7/74; G06T 7/97; G06T 2207/30068; A61B 6/502; A61B 6/5217
See application file for complete search history.

(56) References Cited

U.S. PATENT DOCUMENTS

| | | |
|---|---|---|
| 2015/0042658 A1 | 2/2015 | Erhard et al. |
| 2021/0393226 A1 | 12/2021 | Koike |
| 2022/0309657 A1* | 9/2022 | Koike ................. G06T 7/0012 |

FOREIGN PATENT DOCUMENTS

| | | | | |
|---|---|---|---|---|
| JP | 2015-515296 A | | 5/2015 | |
| JP | 2015-177928 A | * | 10/2015 | ............. A61B 6/025 |
| JP | 2020-512130 A | * | 4/2020 | ............. A61B 6/502 |
| WO | 2010/059920 A2 | | 5/2010 | |
| WO | 2018/183548 A1 | | 10/2018 | |
| WO | 2020/202612 A1 | | 10/2020 | |

OTHER PUBLICATIONS

Extended European Search Report dated Aug. 5, 2022, issued in corresponding EP Patent Application No. 22162221.0.

* cited by examiner

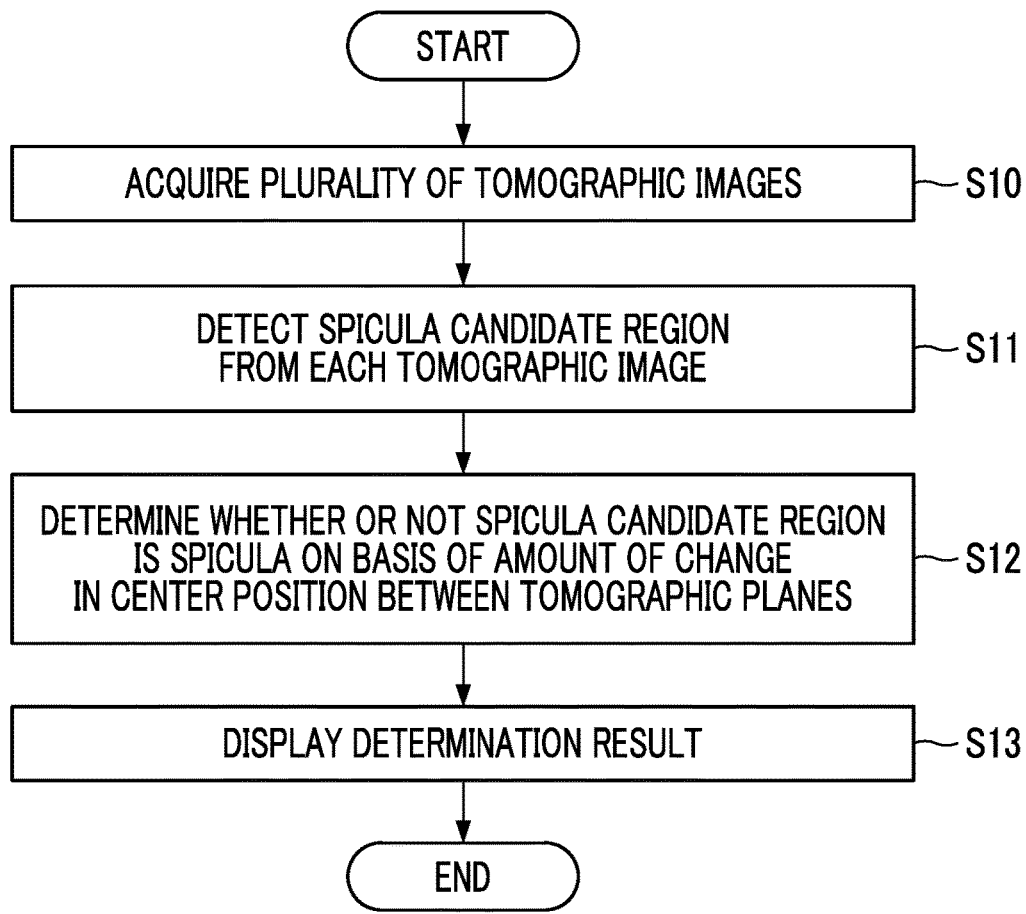
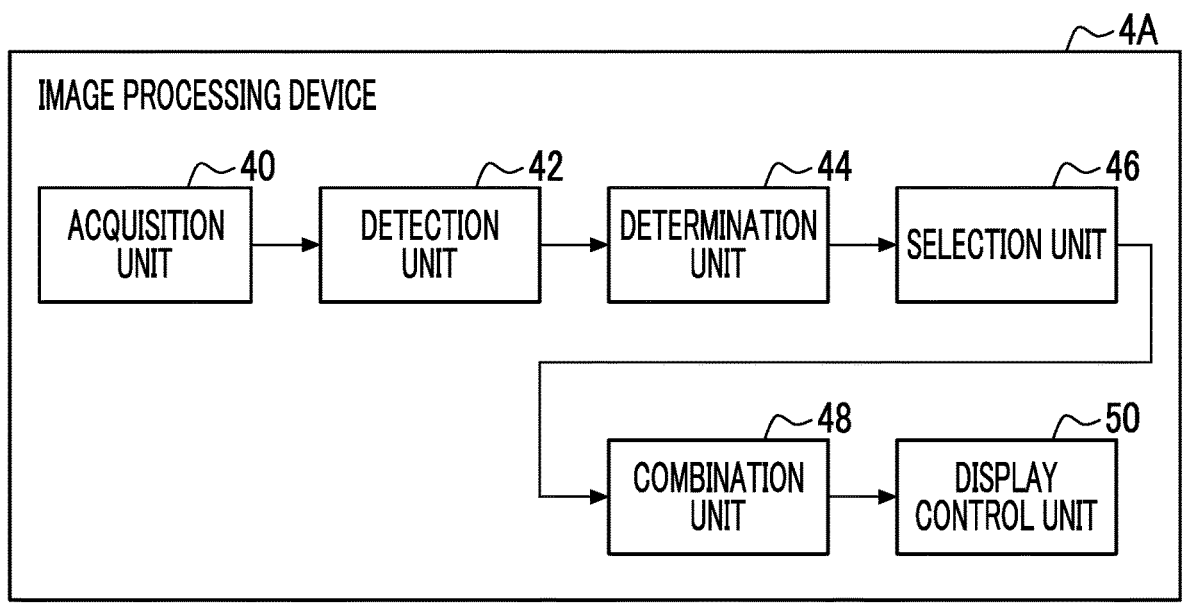

IMAGE PROCESSING DEVICE, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2021-056179 filed on Mar. 29, 2021. The above application is hereby expressly incorporated by reference, in its entirety, into the present application.

BACKGROUND

1. Technical Field

The present disclosure relates to an image processing device, an image processing method, and an image processing program.

2. Description of the Related Art

In recent years, image diagnosis using a radiography apparatus (called mammography) for capturing an image of a breast has attracted attention in order to promote early detection of breast cancer. Further, in the mammography, tomosynthesis imaging has been proposed which moves a radiation source, irradiates the breast with radiation at a plurality of radiation source positions to acquire a plurality of projection images, and reconstructs the acquired plurality of projection images to generate tomographic images in which desired tomographic planes have been highlighted. In the tomosynthesis imaging, the radiation source is moved in parallel to a radiation detector or is moved to draw a circular or elliptical arc, according to the characteristics of an imaging apparatus and the required tomographic images, and the breast is imaged at a plurality of radiation source positions to acquire a plurality of projection images. Then, the acquired plurality of projection images are reconstructed, using a back projection method, such as a simple back projection method or a filtered back projection method, or an iterative reconstruction method, to generate tomographic images.

The tomographic images are generated in a plurality of tomographic planes of the breast, which makes it possible to separate structures that overlap each other in a depth direction in which the tomographic planes are arranged in the breast. Therefore, it is possible to find an abnormal part, such as a lesion, that has been difficult to detect in a two-dimensional image (hereinafter, referred to as a simple two-dimensional image) acquired by simple imaging according to the related art which irradiates an object with radiation in a predetermined direction.

In addition, a technique is known which combines a plurality of tomographic images having different distances (positions in a height direction) from a detection surface of a radiation detector to a radiation source, which have been acquired by tomosynthesis imaging, using, for example, an addition method, an averaging method, a maximum intensity projection method, or a minimum intensity projection method, to generate a pseudo two-dimensional image (hereinafter, referred to as a "composite two-dimensional image") corresponding to the simple two-dimensional image (see JP2014-128716A).

In addition, a technique is known which discriminates an object that is a candidate for a lesion or the like from three-dimensional volume data, tags tomographic images, and performs forward projection on a plurality of tagged tomographic images to generate a composite two-dimensional image, in order to improve the discrimination of the lesion or the like (see JP2015-515296A).

SUMMARY

However, JP2015-515296A does not disclose a technique which detects a spicula that is a candidate for a lesion or the like. The spicula is a radial line structure that is generated by drawing surrounding tissues while breast cancer is growing. Some normal mammary glands have a radial structure that is confusable with the spicula. In general, it is not easy to distinguish between the spicula and the normal mammary gland with one tomographic image. Therefore, analysis using a three-dimensional image is performed. In JP2015-515296A, three-dimensional analysis is also performed in order to discriminate an object that is a candidate for a lesion or the like from a three-dimensional image (3D volume data). The three-dimensional analysis has a problem that it takes a lot of time to perform processes.

The present disclosure has been made in view of the above circumstances, and an object of the present disclosure is to provide an image processing device, an image processing method, and an image processing program that can accurately detect a spicula in a short processing time.

According to an aspect of the present disclosure, there is provided an image processing device comprising at least one processor. The processor detects a spicula candidate region having a radial line structure from each of a plurality of tomographic images indicating a plurality of tomographic planes of an object, and determines whether or not the spicula candidate region is a spicula on the basis of an amount of change of a center position of the line structure included in the spicula candidate region between the tomographic planes.

Preferably, the processor determines the spicula candidate region, in which a variation of the center position of the line structure in an in-tomographic-plane direction is within a reference range, to be the spicula.

Preferably, the processor performs control to display the tomographic image, and performs control to display a result of determining whether or not the spicula candidate region is the spicula on the tomographic image.

Preferably, the processor selects a plurality of the tomographic images including the spicula candidate region determined to be the spicula as a tomographic image group, and generates a composite two-dimensional image using the selected tomographic image group.

Preferably, the processor performs control to display the composite two-dimensional image and performs control to display a result of determining whether or not the spicula candidate region is the spicula on the composite two-dimensional image.

According to another aspect of the present disclosure, there is provided an image processing method that is executed by a processor included in an image processing device. The image processing method comprises: detecting a spicula candidate region having a radial line structure from each of a plurality of tomographic images indicating a plurality of tomographic planes of an object; and determining whether or not the spicula candidate region is a spicula on the basis of an amount of change of a center position of the line structure included in the spicula candidate region between the tomographic planes.

According to another aspect of the present disclosure, there is provided an image processing program that causes a processor included in an image processing device to execute a process comprising: detecting a spicula candidate region having a radial line structure from each of a plurality of tomographic images indicating a plurality of tomographic planes of an object; and determining whether or not the spicula candidate region is a spicula on the basis of an amount of change of a center position of the line structure included in the spicula candidate region between the tomographic planes.

According to the present disclosure, it is possible to provide an image processing device, an image processing method, and an image processing program that can accurately detect a spicula in a short processing time.

BRIEF DESCRIPTION OF THE DRAWINGS

Exemplary embodiments according to the technique of the present disclosure will be described in detail based on the following figures, wherein:

FIG. 10 is a flowchart illustrating an example of a spicula detection process, FIG. 11 is a block diagram illustrating a functional configuration of an image processing device according to a modification example.

DETAILED DESCRIPTION

Hereinafter, an embodiment for carrying out the technology of the present disclosure will be described in detail with reference to the drawings.

Figure 1:
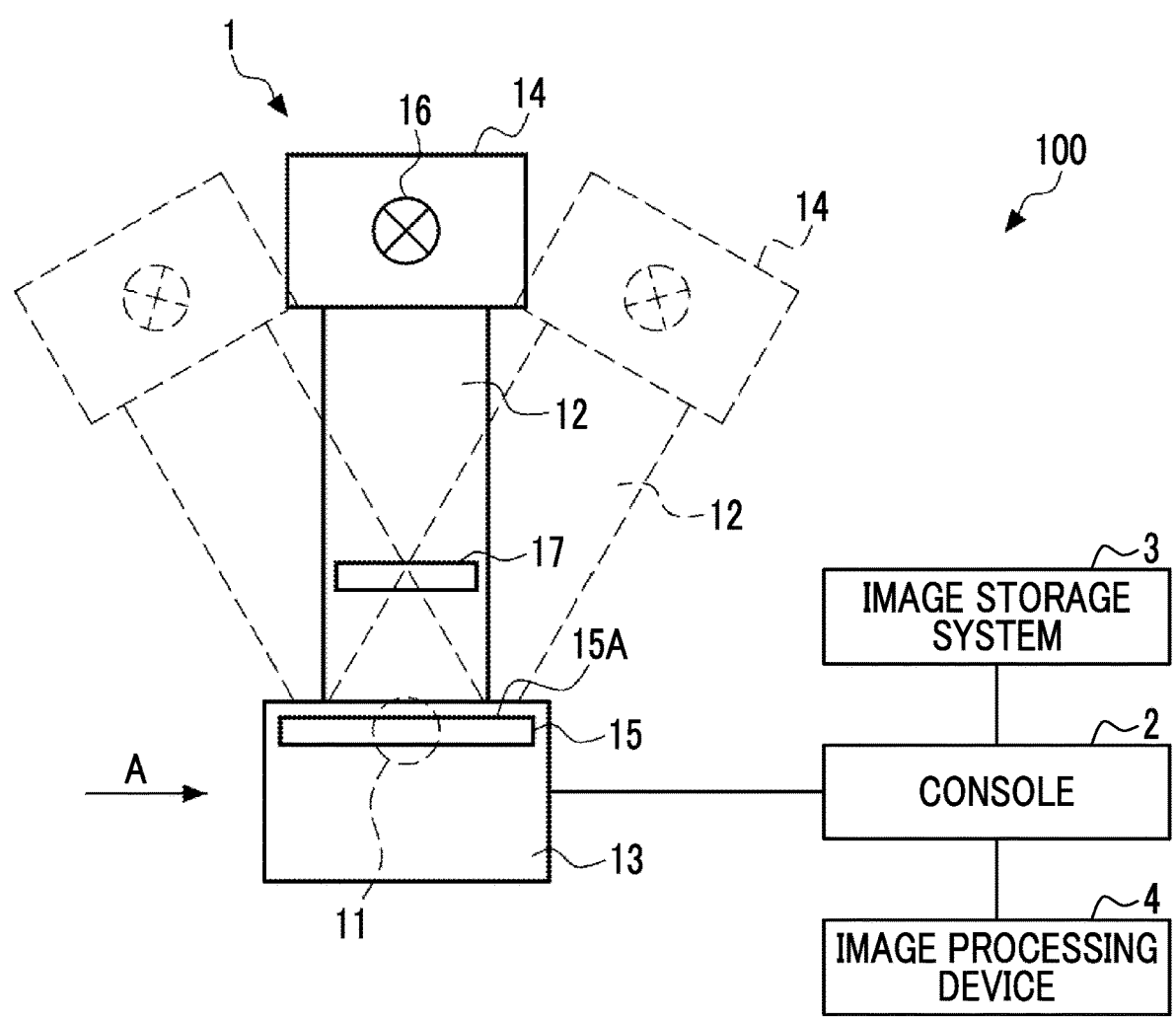
FIG. 1 is a diagram schematically illustrating a configuration of a radiography system.
Figure 2:
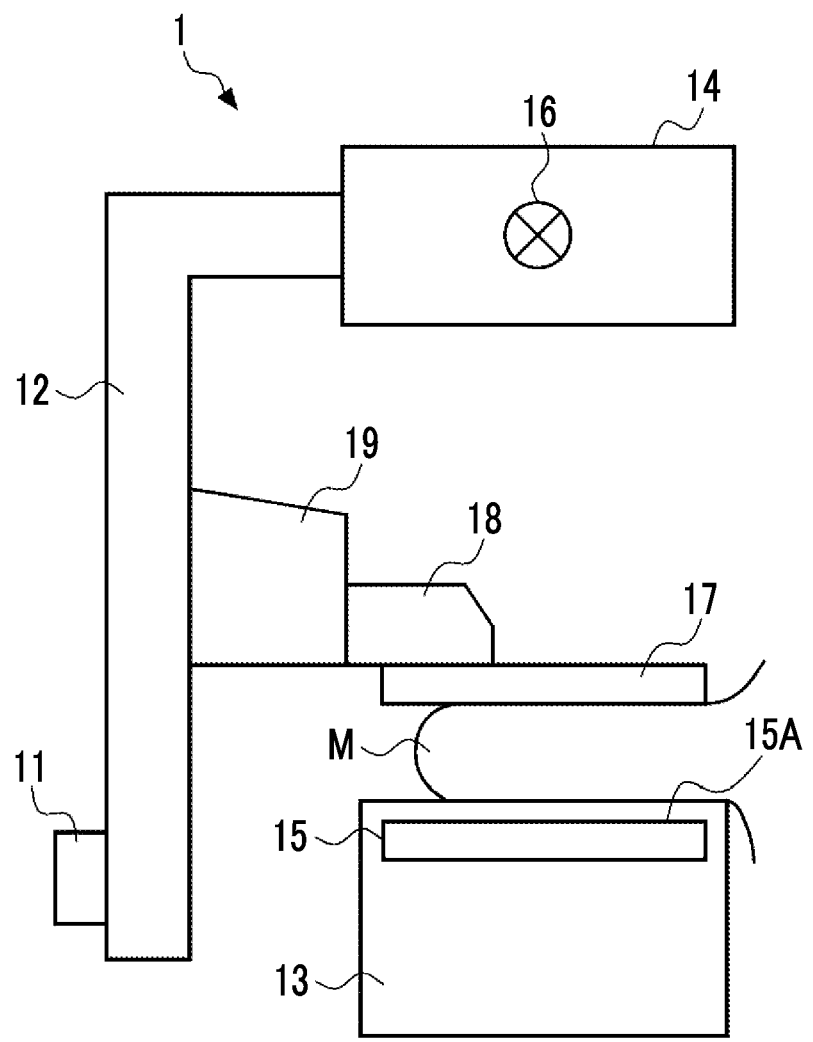
FIG. 2 is a diagram illustrating a radiography apparatus as viewed from a direction of an arrow A in FIG. 1.

First, the configuration of a radiography system 100 according to this embodiment will be described with reference to FIGS. 1 and 2. As illustrated in FIGS. 1 and 2, the radiography system 100 images a breast M, which is an object, at a plurality of radiation source positions and acquires a plurality of radiographic images, that is, a plurality of projection images, in order to perform tomosynthesis imaging on the breast to generate tomographic images. The radiography system 100 comprises a mammography apparatus 1, a console 2, an image storage system 3, and an image processing device 4.

The mammography apparatus 1 comprises an arm portion 12 that is connected to a base (not illustrated) by a rotation shaft 11. An imaging table 13 is attached to one end of the arm portion 12, and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed, and only the radiation emitting unit 14 can be rotated.

A radiation detector 15, such as a flat panel detector, is provided in the imaging table 13. The radiation detector 15 has a radiation detection surface 15A. In addition, for example, a circuit substrate including a charge amplifier that converts a charge signal read out from the radiation detector 15 into a voltage signal, a correlated double sampling circuit that samples the voltage signal output from the charge amplifier, and an analog-to-digital (AD) conversion unit that converts the voltage signal into a digital signal is provided in the imaging table 13.

A radiation source 16 is accommodated in the radiation emitting unit 14. The radiation source 16 emits X-rays as radiation. The console 2 controls the timing when the radiation source 16 emits the radiation and radiation generation conditions (for example, a tube voltage and an irradiation time) of the radiation source 16.

Further, the arm portion 12 is provided with a compression plate 17 that is disposed above the imaging table 13 and compresses the breast M, a support portion 18 that supports the compression plate 17, and a movement mechanism 19 that moves the support portion 18 in an up-down direction. Furthermore, an interval between the compression plate 17 and the imaging table 13, that is, the thickness of the compressed breast is input to the console 2.

The console 2 has a function of controlling the mammography apparatus 1 using, for example, an imaging order and various kinds of information acquired from a radiology information system (RIS) (not illustrated) or the like through a network, such as a wireless communication local area network (LAN), and instructions or the like directly issued by an engineer or the like. Specifically, the console 2 directs the mammography apparatus 1 to perform the tomosynthesis imaging on the breast M, acquires a plurality of projection images as described below, and reconstructs the plurality of projection images to generate a plurality of tomographic images. For example, in this embodiment, a server computer is used as the console 2.

The image storage system 3 is a system that stores image data such as radiographic images and tomographic images captured by the mammography apparatus 1. The image storage system 3 extracts image data corresponding to a request from, for example, the console 2 and the image processing device 4 from the stored image data and transmits the image data to a device that is the source of the request. A specific example of the image storage system 3 is a picture archiving and communication system (PACS).

Figure 3:
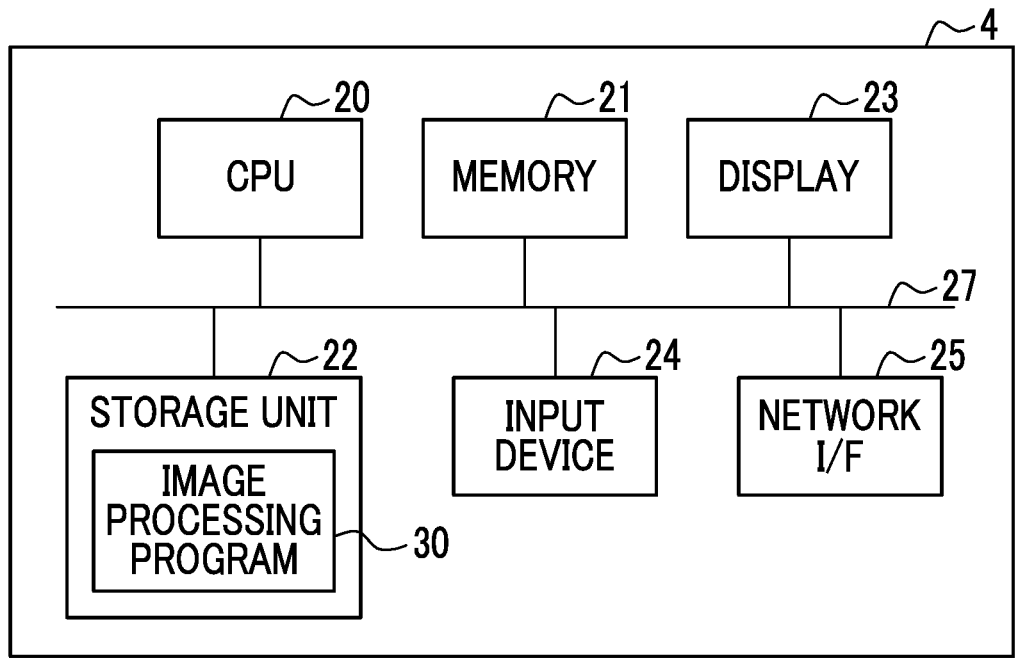
FIG. 3 is a block diagram illustrating an example of a hardware configuration of an image processing device.

Next, the hardware configuration of the image processing device 4 according to this embodiment will be described with reference to FIG. 3. As illustrated in FIG. 3, the image processing device 4 includes a central processing unit (CPU) 20, a memory 21 as a temporary storage area, and a non-volatile storage unit 22. In addition, the image processing device 4 includes a display 23, such as a liquid crystal display, an input device 24, such as a keyboard and a mouse, and a network interface (I/F) 25 that is connected to the network. The CPU 20, the memory 21, the storage unit 22, the display 23, the input device 24, and the network I/F 25 are connected to a bus 27. The CPU 20 is an example of a "processor" according to the technology of the present disclosure.

The storage unit 22 is implemented by, for example, a hard disk drive (HDD), a solid state drive (SSD), or a flash memory. An image processing program 30 is stored in the storage unit 22 as a storage medium. The CPU 20 reads out the image processing program 30 from the storage unit 22, expands the image processing program 30 in the memory 21, and executes the expanded image processing program 30.

Figure 4:
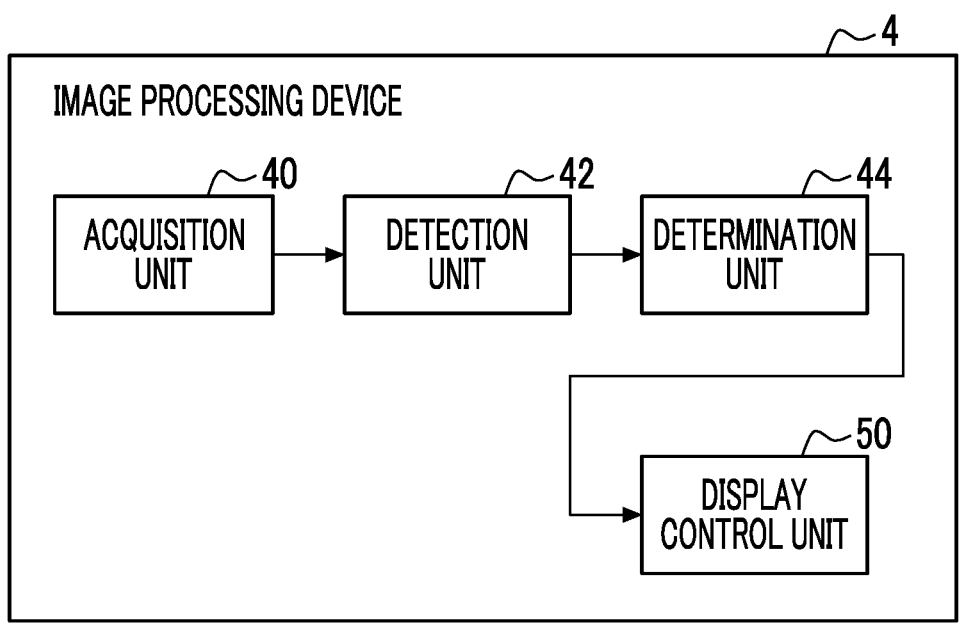
FIG. 4 is a block diagram illustrating an example of a functional configuration of the image processing device.

Next, the functional configuration of the image processing device 4 according to this embodiment will be described with reference to FIG. 4. As illustrated in FIG. 4, the image processing device 4 includes an acquisition unit 40, a detection unit 42, a determination unit 44, and a display control unit 50. The CPU 20 executes the image processing program 30 to function as the acquisition unit 40, the detection unit 42, the determination unit 44, and the display control unit 50.

The acquisition unit 40 acquires a plurality of tomographic images generated by the tomosynthesis imaging performed by the mammography apparatus 1 under the control of the console 2. The acquisition unit 40 acquires a plurality of tomographic images from the console 2 or the image storage system 3 through the network I/F 25.

Here, the tomosynthesis imaging and a tomographic image generation process in the console 2 will be described. The console 2 rotates the arm portion 12 on the rotation shaft 11 to move the radiation source 16 in a case in which the tomosynthesis imaging for generating tomographic images is performed. Further, the console 2 performs control to irradiate the breast M, which is the object, with the radiation under predetermined imaging conditions for tomosynthesis imaging at a plurality of radiation source positions by the movement of the radiation source 16. Further, the console 2 acquires a plurality of projection images Gi (i=1 to n; n is the number of radiation source positions, for example, n=15) at the plurality of radiation source positions which have been obtained by the detection of the radiation transmitted through the breast M by the radiation detector 15.

Figure 5:
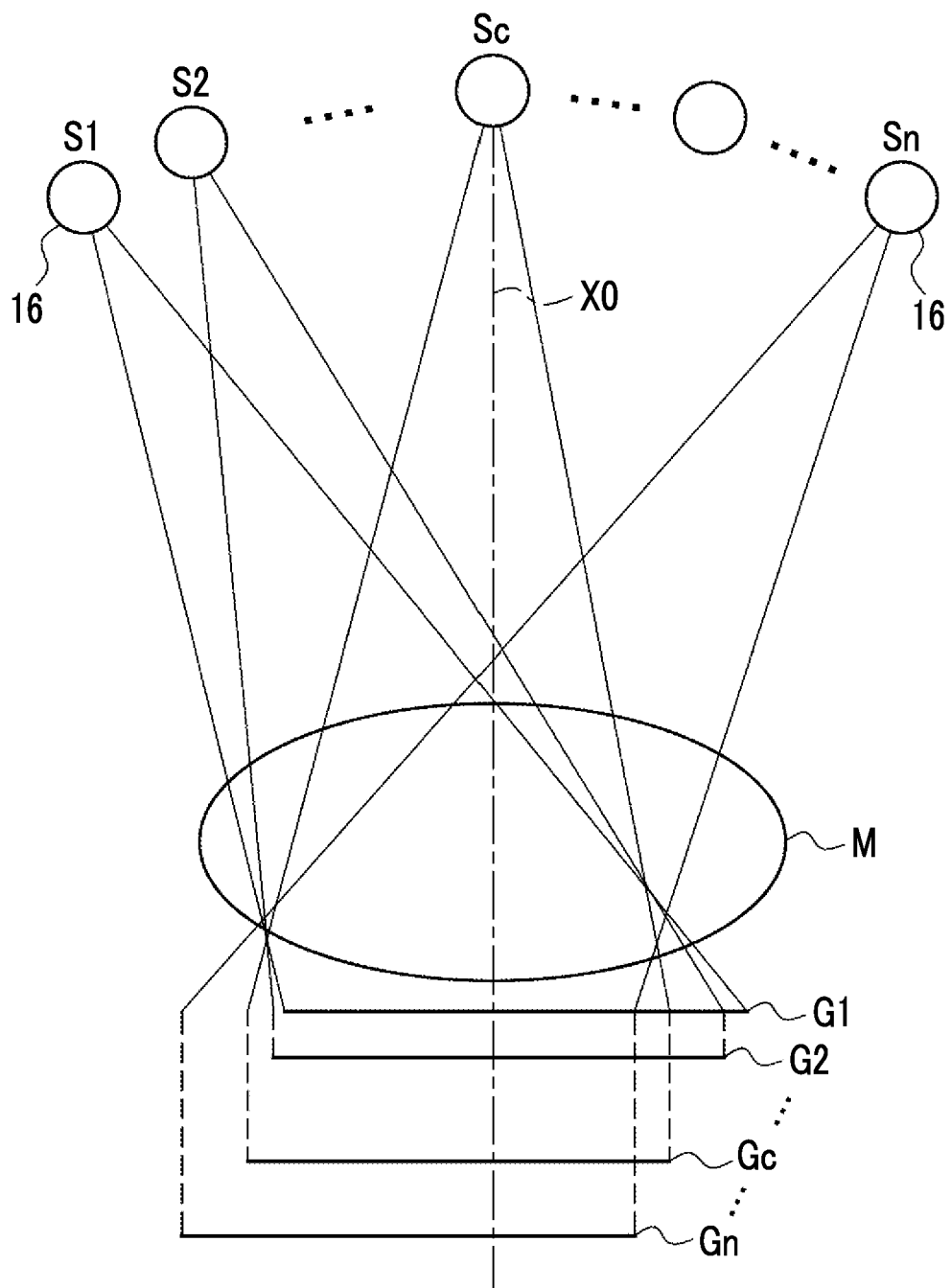
FIG. 5 is a diagram illustrating a projection image acquisition process.

As illustrated in FIG. 5, the radiation source 16 is moved to each of radiation source positions Si (i=1 to n). Then, the radiation source 16 is driven at each of the radiation source positions to emit the radiation to the breast M. In a case in which the radiation detector 15 detects the radiation transmitted through the breast M to acquire the projection images G1, G2, . . . , Gn corresponding to the radiation source positions Si to Sn, respectively. In addition, the same dose of radiation is emitted to the breast M at each of the radiation source positions Si to Sn.

Here, in FIG. 5, a radiation source position Sc is a radiation source position where an optical axis X0 of the radiation emitted from the radiation source 16 is orthogonal to the detection surface 15A of the radiation detector 15. Hereinafter, the radiation source position Sc is referred to as a reference radiation source position Sc.

Figure 6:
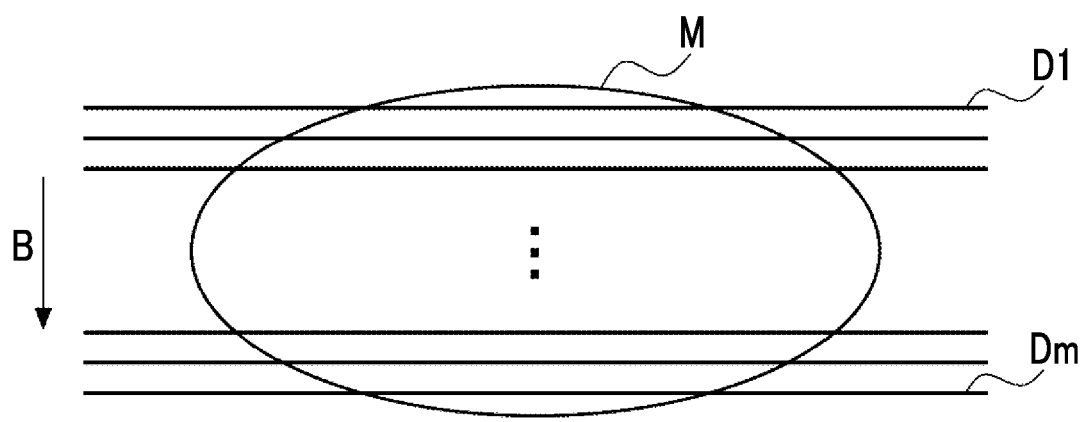
FIG. 6 is a diagram illustrating a tomographic image generation process.

The console 2 reconstructs the plurality of projection images Gi to generate a plurality of tomographic images in which the desired tomographic planes of the breast M have been highlighted. Specifically, the console 2 reconstructs the plurality of projection images Gi using a well-known back projection method such as a simple back projection method or a filtered back projection method. Therefore, as illustrated in FIG. 6, the console 2 generates a plurality of tomographic images Dj (j=1 to m) indicating each of a plurality of tomographic planes of the breast M. In this case, a three-dimensional coordinate position in a three-dimensional space including the breast M is set, and the pixel values of the corresponding pixels in the plurality of projection images Gi are reconstructed for the set three-dimensional coordinate position to calculate a pixel value at the coordinate position. In addition, an arrow B illustrated in FIG. 6 indicates a tomographic depth direction which is a direction orthogonal to the tomographic plane.

The console 2 transmits the generated tomographic images Dj to the image processing device 4 or the image storage system 3.

Figure 7:
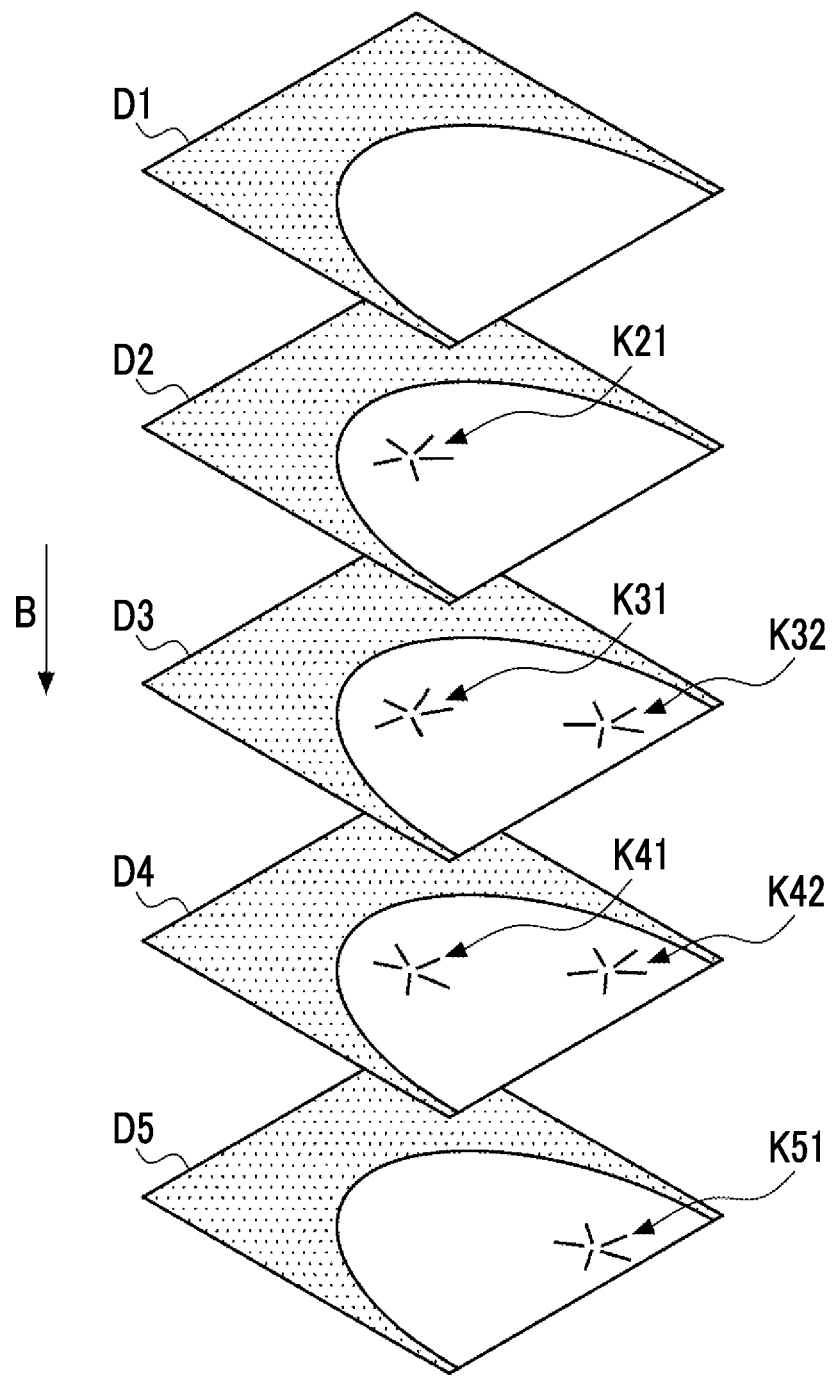
FIG. 7 is a diagram illustrating an example of a plurality of tomographic images.

For example, as illustrated in FIG. 7, the detection unit 42 detects a region including a spicula candidate (hereinafter, referred to as a spicula candidate region) from each of the plurality of tomographic images Dj acquired by the acquisition unit 40. A spicula is a radial line structure (hereinafter, referred to as a radial structure) that is generated by drawing surrounding tissues while breast cancer is growing. The detection unit 42 detects, as the spicula candidate region, a region including line structures that extend radially from each of the tomographic images Dj. Further, in the tomographic image, a normal mammary gland is likely to appear as the radial structure similar to the spicula. Therefore, the spicula candidate region is likely to include the normal mammary gland.

FIG. 7 illustrates a case in which the number of tomographic images Dj is 5 (that is, j=1 to 5) for simplicity of description. In the example illustrated in FIG. 7, a tomographic image D2 includes a spicula candidate region K21, a tomographic image D3 includes a spicula candidate region K31 and a spicula candidate region K32, a tomographic image D4 includes a spicula candidate region K41 and a spicula candidate region K42, and a tomographic image D5 includes a spicula candidate region K51.

The detection unit 42 detects the spicula candidate region from each of the plurality of tomographic images Dj using a known algorithm for detecting a spicula using computer aided diagnosis (CAD). In the algorithm for detecting a spicula using CAD, a probability (likelihood) indicating that a pixel in the tomographic image Dj is the spicula candidate region is derived, and a pixel with a probability equal to or greater than a predetermined threshold value is detected as the spicula candidate region. It is difficult to distinguish between the spicula and the normal mammary gland that extends radially with only one tomographic image Dj. Therefore, the normal mammary gland that extends radially is also detected as the spicula candidate region.

In addition, a process of detecting the spicula candidate region is not limited to the process using CAD. For example, the process of detecting the spicula candidate region may be a process of detecting the spicula candidate region from the tomographic images Dj with a filtering process using a filter (for example, a radial filter). Further, the process of detecting the spicula candidate region may be a process of detecting the spicula candidate region from the tomographic images Dj with a detection model or the like that has been subjected to machine learning by deep learning or the like.

Figure 8:
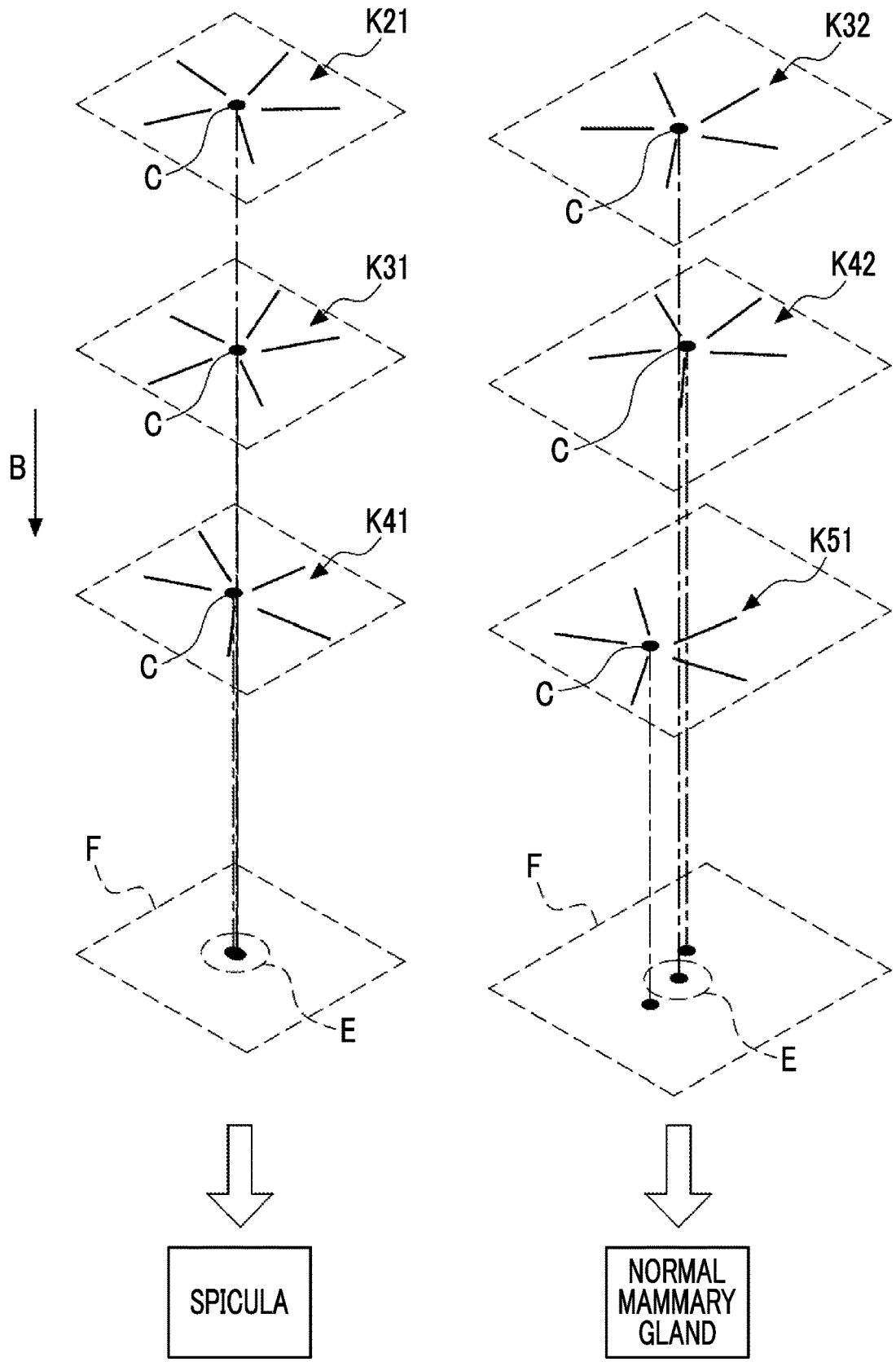
FIG. 8 is a diagram illustrating a spicula candidate region determination process.

The determination unit 44 determines whether or not the spicula candidate region is the spicula on the basis of the amount of change of the center position of the radial structure included in the spicula candidate region between the tomographic planes. Specifically, as illustrated in FIG. 8, the determination unit 44 selects a plurality of spicula candidate regions having substantially the same position in the tomographic images Dj among the plurality of spicula candidate regions detected by the detection unit 42 and specifies a center position C of each of the selected plurality of spicula candidate regions. Then, the determination unit 44 determines the spicula candidate region, in which a variation of the specified center position C in an in-tomographic-plane direction is within a reference range E, to be the "spicula".

Here, "substantially the same position in the tomographic images Dj" means that, for example, at least portions of the spicula candidate regions overlap between the tomographic images. Further, the center position C is a position where radial line structures converge. Furthermore, the variation of the center position C in the in-tomographic-plane direction is, for example, a dispersion value.

In the example illustrated in FIG. 8, the determination unit 44 projects each of the center positions C of spicula candidate regions K21, K31, and K41 having substantially the same position in the tomographic images Dj onto a virtual plane F that is parallel to the tomographic planes and calculates a variation of the projected center position C in the virtual plane F. The spicula candidate regions K21, K31, and K41 are determined to be the spicula since the variation of the center position C is within the reference range E.

Similarly, the determination unit 44 projects each of the center positions C of spicula candidate regions K32, K42, and K51 having substantially the same position in the tomographic images Dj onto the virtual plane F that is parallel to the tomographic planes and calculates a variation of the projected center position C in the virtual plane F. The spicula candidate regions K32, K42, and K51 are determined to be the normal mammary gland since the variation of the center position C is not within the reference range E.

The spicula is a radial structure that is generated by drawing the surrounding tissues while breast cancer is growing. Therefore, lines extend radially from the nucleus of the breast cancer in any tomographic image. That is, in the spiculae, the center positions of the radial structures are substantially aligned with each other between the tomographic images. In contrast, the normal mammary gland similar to the spicula has lines that extend radially, but does not have the nucleus unlike breast cancer. Therefore, in the normal mammary glands, the center position of the radial structure changes between the tomographic images in the tomographic planes. The determination unit 44 performs the above-described determination using this feature.

Figure 9:
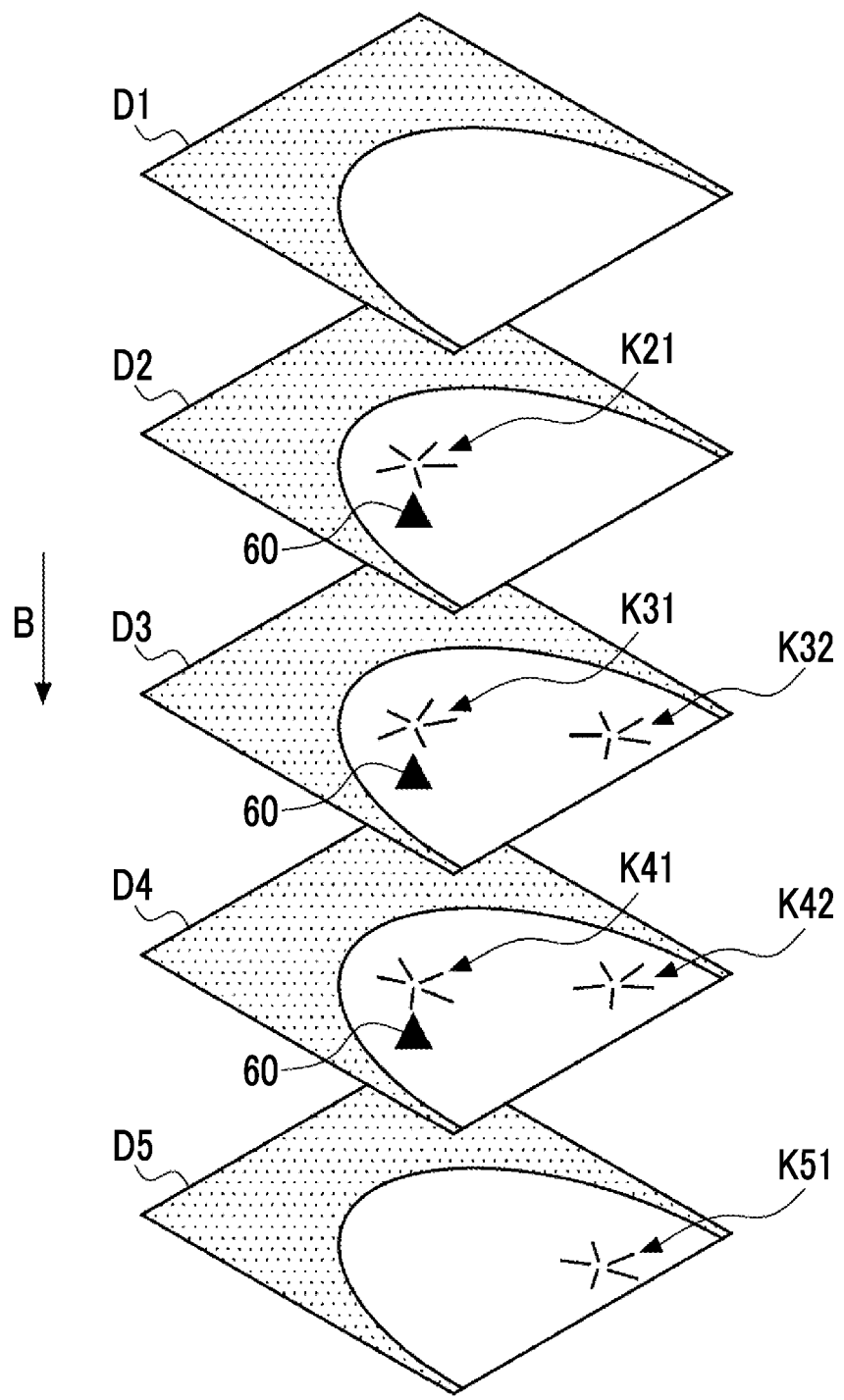
FIG. 9 is a diagram illustrating an example of a display state of a determination result.

In addition, the display control unit 50 performs control to display the determination result of the spicula candidate region by the determination unit 44 on the display 23. For example, the display control unit 50 performs control to display the tomographic images Dj and to display the determination result on the tomographic images Dj. FIG. 9 illustrates an example of the display state of the determination result. As illustrated in FIG. 9, the display control unit 50 performs control to display a mark 60 indicating the determination result by the determination unit 44 in the vicinity of the spicula candidate region to be determined. In the example illustrated in FIG. 9, the triangular mark 60 is displayed in the vicinity of the spicula candidate region determined to be the spicula.

Next, the operation of the image processing device 4 according to this embodiment will be described with reference to FIG. 10. The CPU 20 executes the image processing program 30 to perform a spicula detection process illustrated in FIG. 10. The spicula detection process illustrated in FIG. 10 is performed, for example, in a case in which the user inputs an execution start instruction through the input device 24.

In Step S10, the acquisition unit 40 acquires a plurality of tomographic images Dj generated by the tomosynthesis imaging performed by the mammography apparatus 1 under the control of the console 2.

In Step S11, as described above, the detection unit 42 detects the spicula candidate region from each of the plurality of tomographic images Dj acquired in Step S10 (see FIG. 7).

In Step S12, as described above, the determination unit 44 determines whether or not the spicula candidate region is the spicula on the basis of the amount of change of the center position of the radial structure included in the spicula candidate region detected in Step S10 between the tomographic planes (see FIG. 8).

In Step S13, as described above, the display control unit 50 performs control to display the tomographic images Dj and to display the determination result on the tomographic images Dj (see FIG. 9). In a case in which the process in Step S13 ends, the spicula detection process ends.

As described above, in the spicula detection process according to this example, the spicula is detected on the basis of the amount of change of the center position of the radial structure included in the spicula candidate region between the tomographic planes. In a case in which the spicula candidate region is the spicula, the amount of change of the center position between the tomographic planes is small. In a case in which the spicula candidate region is the normal mammary gland, the amount of change of the center position between the tomographic planes is large. Therefore, it is possible to accurately detect the spicula.

As described above, according to this embodiment, the spicula candidate region is detected from the tomographic images. Therefore, it is possible to detect the spicula in a short processing time as compared to a case in which a candidate for, for example, a lesion is detected from a three-dimensional image (3D volume data) as in the related art. That is, according to this embodiment, it is possible to accurately detect the spicula in a short processing time, and an interpretation burden on a diagnostician, such as a doctor, is reduced.

In the above-described embodiment, the display control unit 50 performs control to display the determination result by the determination unit 44 with the mark 60. However, the display control unit 50 may perform control to display the determination result by the determination unit 44 such that the color of the spicula candidate region indicating the determination result is different from the colors of other regions. In addition, the display control unit 50 may perform control to display a character string indicating the determination result by the determination unit 44 in the vicinity of the spicula candidate region indicating the determination result.

Modification Example

Next, a modification example of the above-described embodiment will be described. In this modification example, a plurality of tomographic images Dj are combined to generate a composite two-dimensional image.

As illustrated in FIG. 11, an image processing device 4A according to this modification example includes an acquisition unit 40, a detection unit 42, a determination unit 44, a selection unit 46, a combination unit 48, and a display control unit 50. The CPU 20 executes the image processing program 30 to function as the acquisition unit 40, the detection unit 42, the determination unit 44, the selection unit 46, the combination unit 48, and the display control unit

50. The acquisition unit 40, the detection unit 42, and the determination unit 44 have the same functions as those in the above-described embodiment.

Figure 12:
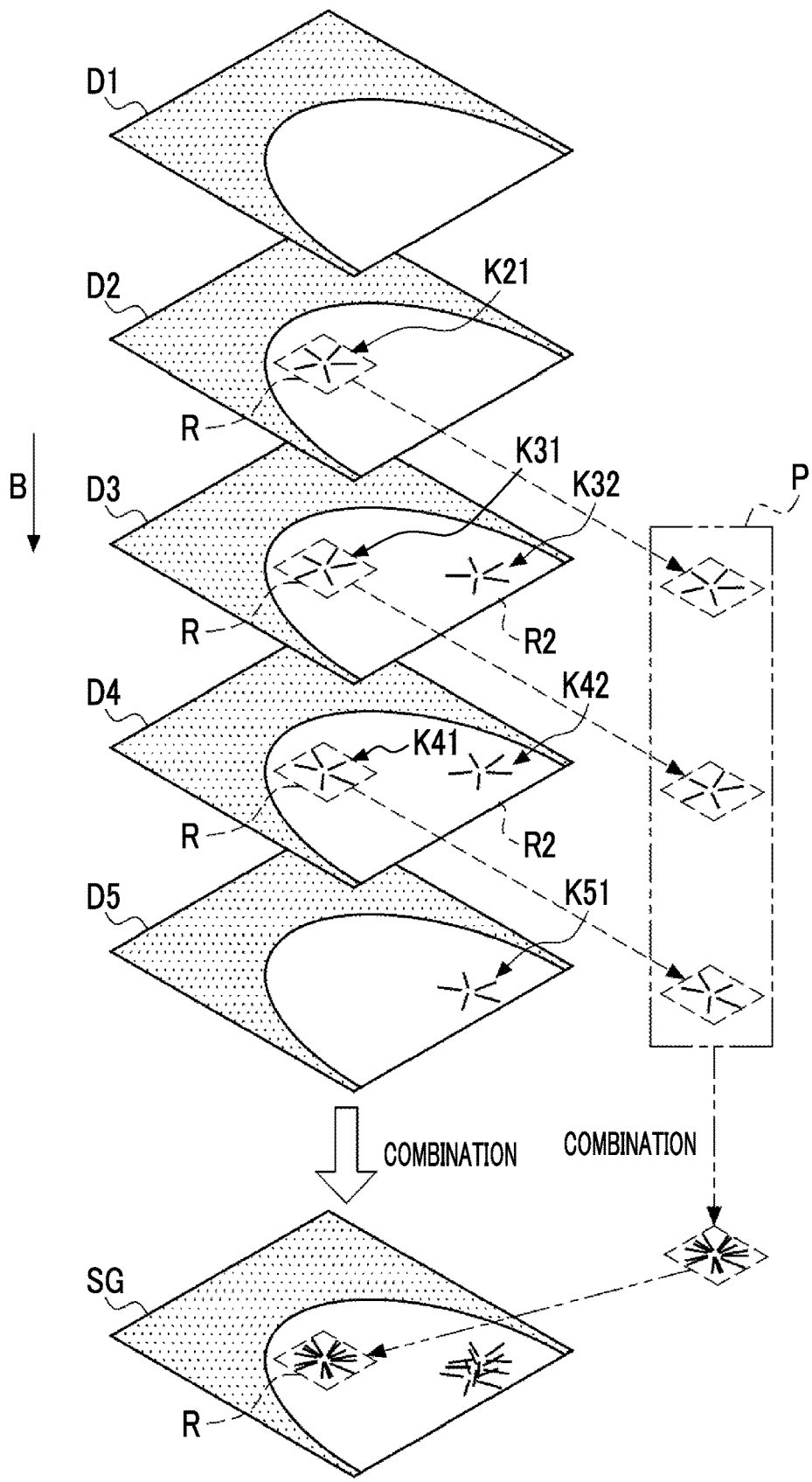
FIG. 12 is a diagram illustrating a tomographic image group selection process.

The selection unit 46 selects, as a tomographic image group P, a plurality of tomographic image Dj including the spicula candidate region determined to be the spicula by the determination unit 44. For example, as illustrated in FIG. 12, in a case in which the determination unit 44 determines that the spicula candidate regions K21, K31, and K41 are the spicula, the selection unit 46 selects tomographic images D2 to D4 as the tomographic image group P. In the following description, a region including the spicula candidate regions K21, K31, and K41 is referred to as a selection region R.

The combination unit 48 generates a composite two-dimensional image SG using the tomographic image group P selected by the selection unit 46. Here, the composite two-dimensional image SG is a pseudo two-dimensional image corresponding to a simple two-dimensional image that is captured by irradiating the breast M with radiation at the reference radiation source position Sc (see FIG. 5). In this embodiment, the combination unit 48 combines the pixel values of the corresponding pixels in each of the tomographic images Dj along a viewing direction from the reference radiation source position Sc to the radiation detector 15, that is, along the optical axis X0 (see FIG. 5) in a state in which the plurality of tomographic images Dj are stacked as illustrated in FIG. 13 to generate the composite two-dimensional image SG Hereinafter, a specific example of a composite two-dimensional image generation process will be described.

Figure 13:
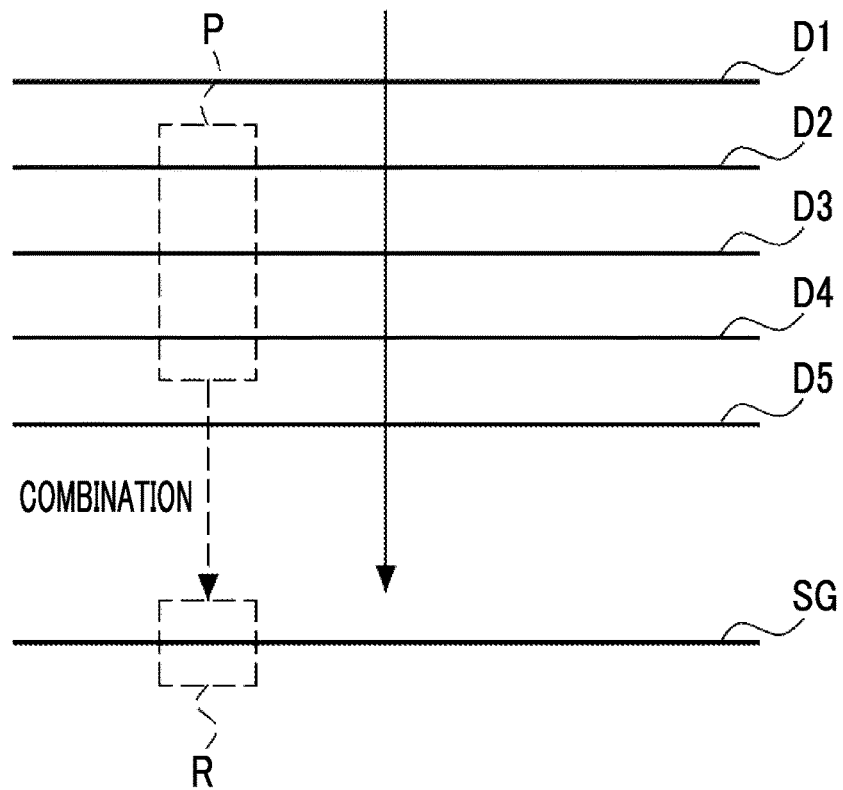
FIG. 13 is a diagram illustrating a composite two-dimensional image generation process.

In this modification example, as illustrated in FIG. 13, the tomographic images D2 to D4 included in the tomographic image group P are combined for the selection region R. All of the tomographic images D1 to D5 are combined for regions other than the selection region R. The combination unit 48 uses an added average value of the pixel values for the corresponding pixel positions in the tomographic image group to be combined as the pixel value of the composite two-dimensional image SG.

Figure 14:
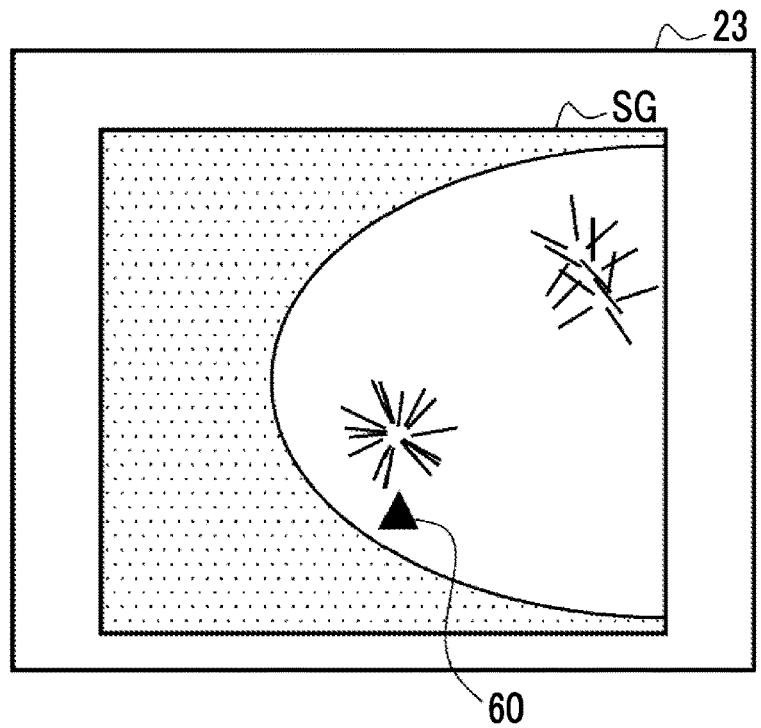
FIG. 14 is a diagram illustrating an example of a display state of a determination result according to the modification example.

In this modification example, the display control unit 50 performs control to display the composite two-dimensional image SG generated by the combination unit 48 on the display 23. Further, in this modification example, the display control unit 50 performs control to display the determination result of the spicula candidate region by the determination unit 44 on the composite two-dimensional image SG FIG. 14 illustrates an example of the display state of the determination result. As illustrated in FIG. 14, the display control unit 50 performs control to display the mark 60 indicating the determination result by the determination unit 44 in the vicinity of the spicula candidate region to be determined. In the example illustrated in FIG. 14, the triangular mark 60 is displayed in the vicinity of the spicula candidate region determined to be the spicula.

The display control unit 50 may perform control to display the determination result by the determination unit 44 such that the color of the spicula candidate region indicating the determination result is different from the color of other regions. In addition, the display control unit 50 may perform control to display a character string indicating the determination result by the determination unit 44 in the vicinity of the spicula candidate region indicating the determination result.

Figure 15:
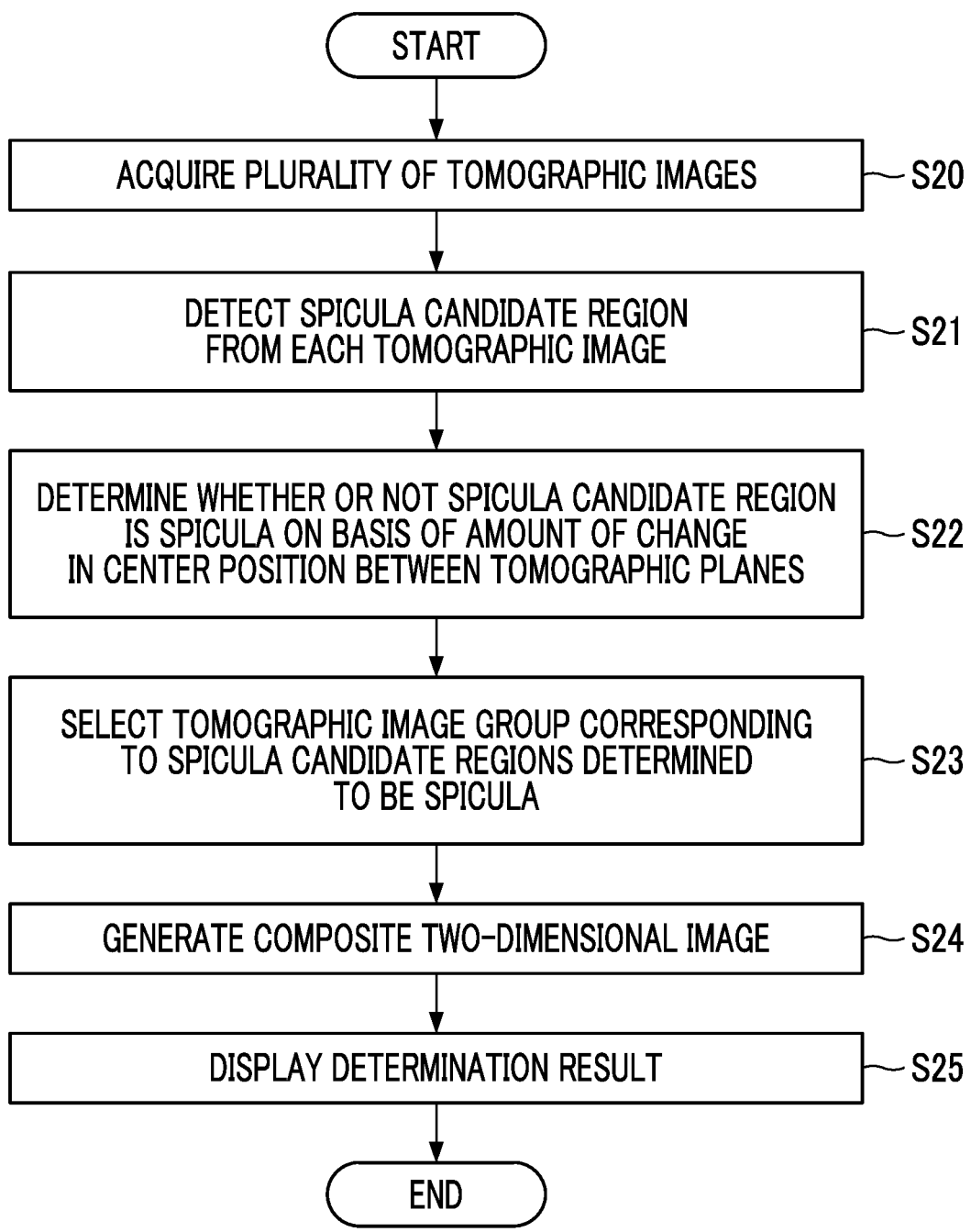
FIG. 15 is a flowchart illustrating an example of a spicula detection process according to the modification example.

Next, the operation of the image processing device 4A according to this modification example will be described with reference to FIG. 15. The CPU 20 executes the image processing program 30 to perform a spicula detection process illustrated in FIG. 15. Since Steps S20 to S22 are the same as Steps S10 to S12 (see FIG. 10) in the above-described embodiment, the description thereof will not be repeated.

In Step S23, as described above, the selection unit 46 selects, as the tomographic image group P, a plurality of tomographic image Dj including the spicula candidate region determined to be the spicula in Step S22 (see FIG. 12).

In Step S24, as described above, the combination unit 48 generates the composite two-dimensional image SG using the tomographic image group P selected by the selection unit 46 (see FIGS. 12 and 13).

In Step S25, as described above, the display control unit 50 performs control to display the composite two-dimensional image SG generated by the combination unit 48 on the display 23 and performs control to display the determination result of the spicula candidate region by the determination unit 44 on the composite two-dimensional image SG (see FIG. 14). In a case in which the process in Step S25 ends, the spicula detection process ends.

In this modification example, a plurality of tomographic images including the spicula candidate region determined to be the spicula are selected as the tomographic image group P, and the composite two-dimensional image SG is generated using the selected tomographic image group P. Therefore, the visibility of the spicula on the composite two-dimensional image SG is improved. As a result, an interpretation burden on a diagnostician, such as a doctor, is reduced.

In addition, in the above-described modification example, the combination unit 48 uses the added average value of the pixel values at the corresponding pixel positions in the tomographic image group P as the pixel value of the composite two-dimensional image SG for the selection regions R including the plurality of spicula candidate regions selected by the selection unit 46. Instead of this configuration, the combination unit 48 may use the added average value of the pixel values of the pixels at the corresponding pixel positions in a plurality of spicula candidate regions having the same plane position in the tomographic images Dj as the pixel value of the composite two-dimensional image SG In the case of this combination, for the pixel at the pixel position included in only one of the plurality of spicula candidate regions, the combination unit 48 uses the pixel value of the pixel as the pixel value of the composite two-dimensional image SG.

Further, in the above-described modification example, the combination unit 48 combines all of the tomographic images included in the tomographic image group P selected by the selection unit 46. However, the combination unit 48 may combine some of the tomographic images included in the tomographic image group P. For example, in the example illustrated in FIG. 12, the combination unit 48 may combine only the tomographic image D2 and the tomographic image D4 among the tomographic images D2 to D4 included in the tomographic image group P. That is, the combination process of the combination unit 48 is not limited to the combination of a plurality of continuous tomographic images and may combine a plurality of discontinuous tomographic images.

Furthermore, in the above-described modification example, the case in which the added average value of the pixel values of the corresponding pixels in the selected tomographic image group is applied as the pixel value of the pixel of the composite two-dimensional image SG has been described. However, the present disclosure is not limited thereto. A weighted average value or a median value, a maximum value, or a minimum value of the pixel values of the corresponding pixels in the selected tomographic image group may be applied as the pixel value of the pixel of the composite two-dimensional image SG Alternatively, a tomographic image having pixels in which a difference between the pixel value of a pixel of interest and an average value of the pixel values of all of the tomographic images in the tomographic image group is larger than a set value, a tomographic image in which a dispersion value of the pixel values of a region of interest including the pixel of interest is larger than that in other regions, or a tomographic image having pixels detected by edge detection may be selectively combined.

Further, in the above-described embodiment, for example, the following various processors can be used as a hardware structure of processing units performing various processes, such as the acquisition unit 40, the detection unit 42, the determination unit 44, and the display control unit 50. Similarly, in the above-described modification example, the following various processors can be used as a hardware structure of processing units performing various processes, such the acquisition unit 40, the detection unit 42, the determination unit 44, the selection unit 46, the combination unit 48, and the display control unit 50.

The various processors include, for example, a CPU which is a general-purpose processor executing software (programs) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the image processing program 30 is stored (installed) in the storage unit 22 in advance has been described. However, the present disclosure is not limited thereto. The image processing program 30 may be recorded on a recording medium, such as a compact disc read only memory (CD-ROM), a digital versatile disc read only memory (DVD-ROM), or a universal serial bus (USB) memory, and then provided. In addition, the image processing program 30 may be downloaded from an external device through a network.

What is claimed is:

1. An image processing device comprising:
   at least one processor,
   wherein the processor detects a spicula candidate region having a radial line structure from each of a plurality of tomographic images indicating a plurality of tomographic planes of an object, and determines whether or not the spicula candidate region is a spicula on the basis of an amount of change of a center position of the line structure included in the spicula candidate region between the tomographic planes.

2. The image processing device according to claim 1,
   wherein the processor determines the spicula candidate region, in which a variation of the center position of the line structure in an in-tomographic-plane direction is within a reference range, to be the spicula.

3. The image processing device according to claim 2,
   wherein the processor performs control to display the tomographic image, and performs control to display a result of determining whether or not the spicula candidate region is the spicula on the tomographic image.

4. The image processing device according to claim 2,
   wherein the processor selects a plurality of the tomographic images including the spicula candidate region determined to be the spicula as a tomographic image group, and generates a composite two-dimensional image using the selected tomographic image group.

5. The image processing device according to claim 4,
   wherein the processor performs control to display the composite two-dimensional image, and performs control to display a result of determining whether or not the spicula candidate region is the spicula on the composite two-dimensional image.

6. An image processing method that is executed by a processor included in an image processing device, the image processing method comprising:
   detecting a spicula candidate region having a radial line structure from each of a plurality of tomographic images indicating a plurality of tomographic planes of an object; and
   determining whether or not the spicula candidate region is a spicula on the basis of an amount of change of a center position of the line structure included in the spicula candidate region between the tomographic planes.

7. A non-transitory computer-readable storage medium storing an image processing program that causes a processor included in an image processing device to execute a process comprising:
   detecting a spicula candidate region having a radial line structure from each of a plurality of tomographic images indicating a plurality of tomographic planes of an object; and
   determining whether or not the spicula candidate region is a spicula on the basis of an amount of change of a center position of the line structure included in the spicula candidate region between the tomographic planes.

* * * * *